(12) United States Patent
Abita et al.

(10) Patent No.: US 6,579,235 B1
(45) Date of Patent: Jun. 17, 2003

(54) METHOD FOR MONITORING INTRAOCULAR PRESSURE USING A PASSIVE INTRAOCULAR PRESSURE SENSOR AND PATIENT WORN MONITORING RECORDER

(75) Inventors: Joseph L. Abita, Boyds, MD (US); Bliss G. Carkhuff, Laurel, MD (US); Roddy Frankel, West Dundee, IL (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/703,402

(22) Filed: Nov. 1, 2000

Related U.S. Application Data

(60) Provisional application No. 60/162,793, filed on Nov. 1, 1999.

(51) Int. Cl.$^7$ .................................................. A61B 3/16
(52) U.S. Cl. ........................ 600/398; 600/561; 600/399; 600/400
(58) Field of Search ................................ 600/398, 399, 600/400, 402, 406, 561, 562, 587; 604/8, 9

(56) References Cited

U.S. PATENT DOCUMENTS

| | | | | |
|---|---|---|---|---|
| 5,005,577 A | * | 4/1991 | Frenkel ........................ | 600/398 |
| 5,433,701 A | * | 7/1995 | Rubinstein ..................... | 604/8 |
| 5,840,041 A | * | 11/1998 | Petter et al. ................. | 600/547 |
| 6,123,668 A | * | 9/2000 | Abreu ........................ | 600/405 |
| 6,193,656 B1 | * | 2/2001 | Jeffries et al. .............. | 600/398 |
| 6,287,256 B1 | * | 9/2001 | Park et al. .................. | 600/398 |

FOREIGN PATENT DOCUMENTS

| EP | 61777 A2 | * 10/1982 | ................. 600/405 |
|---|---|---|---|

OTHER PUBLICATIONS

Backlund, Y., et al., "Passive Silicon Transensor Intended for Biomedical, Remote Pressure Monitoring," Sensors and Actuators, A21–A23, pp. 58–61 (1990).*

Rosengren, L., et al., "A System for Wireless Intro–Ocular Pressure Measurements Using a Silicon Micromachined Sensor," J. of Micromech. Microeng., vol. 2, pp. 202–204 (1992).*

Rosengren, L., et al., "A System for Passive Implantable Pressure Sensors," Sensors and Actuators, A, pp. 1–4 (1994).*

* cited by examiner

*Primary Examiner*—Charles A. Marmor, II
(74) *Attorney, Agent, or Firm*—Benjamin Y. Rocas, Esq.

(57) ABSTRACT

A device for passively measuring intraocular pressure of a patient including an in vivo sensor and an instrument external to the patient for remotely energizing the sensor, thereby permitting the instrument to determine the intraocular pressure. The device directly and continuously measures the intraocular pressure of a patient. The in vivo sensor in the intraocular pressure monitor includes a capacitive pressure sensor and an inductive component. An instrument, external to the patient, measures the pressure, provides readout of the pressure values and determines the intraocular pressure.

2 Claims, 12 Drawing Sheets

METHOD FOR MONITORING INTRAOCULAR PRESSURE USING A PASSIVE INTRAOCULAR PRESSURE SENSOR AND PATIENT WORN MONITORING RECORDER

CROSS-REFERENCE TO RELATED APPLICATIONS

This application claims the benefit of U.S. provisional application No. 60/162,793, filed on Nov. 1, 1999.

BACKGROUND OF THE INVENTION

1. Field of the Invention

The invention relates to a method and device for monitoring intraocular pressure. Intraocular pressure, the pressure of fluid within an eye, takes on significance with respect to glaucoma and its treatment.

The glaucomas are a group of diseases that constitute a public health problem of staggering proportions. An estimated 5–10 million Americans have an intraocular pressure (IOP) greater than 21 mm Hg on routine office testing, placing them at increased risk of suffering glaucomatous optic nerve damage. Conservatively estimated, approximately 2 million Americans have glaucoma, while only 1 million patients are undergoing treatment. Nine hundred thousand Americans have some degree of vision impairment, and 80,000 patients are legally blind as a result of glaucoma.

Many factors are known to influence IOP, which accounts for the wide fluctuations noted in both the normal and glaucomatous population. Diurnal variation in IOP may frequently reach 6 mm Hg, and daily pressure peaks may reach 30 mm or more. Pressure spikes resulting from eye squeezing or rubbing can reach much higher levels. These pressure peaks may not be detected clinically, thus resulting in misdiagnosed, or undiagnosed glaucoma. Some glaucoma patients carry the diagnosis of normal tension glaucoma. While this group of diseases may represent an abnormal sensitivity of the optic nerve to seemingly normal IOP, it may also represent an inadequate sampling of IOP, which misses periods of significant IOP elevation. Thus, at least a subgroup of glaucoma patients may not be diagnosed, or treated, until a significant progression in their disease has been detected. The optimal frequency for measuring IOP has yet to be determined. Routine office visits are often spaced 3–4 months apart. Visits are more frequent during periods of medication adjustment. Following eye surgery, IOP measurements may be required every few hours. More than 3 million office visits each year are devoted to monitoring IOP in patients who are either being treated for glaucoma, or who are suspected of having glaucoma. Substantial healthcare resources are devoted to the task of monitoring IOP, and even this effort may represent a sub-optimal surveillance strategy.

2. Description of the Related Art

As a physiological parameter, IOP is important in its correlation with ocular fluid mechanics, muscular action, hemodynamics, and glaucoma diseases. For over three decades, medical, biomedical, and engineering professionals have been developing methods, devices and instruments to obtain accurate measurements of dynamic intraocular pressure. Conventional ophthalmotonometers (COT) are useful to this end, but, in general, they do not offer the features desired for certain ocular research and therapy. The medical needs are to continuously and "conveniently" monitor internal-to-the eye hydrostatic pressure in ambulatory subjects—these attributes are lacking in COT.

One of the earliest attempts to obtain accurate measurements of intraocular pressure by direct contact with the internal fluids of the eye is described by Collins, Miniature Passive Transensor for Implanting in the Eye, IEEE TRANSACTIONS ON BIO-MEDICAL ENGINEERING, Vol. BME-14, No 2, April 1967.

Work in this area during the following two decades indicates the continued need for and interest in obtaining dynamic, real-time intraocular pressure measurements. Few of the advances in this area take a direct measurement of the eye's internal pressure, that is, by having the hydrostatic pressure of eye fluids acting directly on a sensor. In most cases, IOP was inferred using various active and passive pressure sensors in contact with the external globe, sclerotic or cornea, of the eye. Examples of active pressure sensors include strain gauge type sensors. Examples of passive pressure sensors include self-resonant type sensors.

More recent efforts are described in Schnell et al., "Measurement of Intraocular Pressure by Telemetry in Conscious Unrestrained Rabbits," INVESTIGATIVE OPHTHALMOLOGY & VISUAL SCIENCE, Vol. 37, No. 6, pp. 958–965, May 1996, and McLaren et al., "Continuous Measurement of Intraocular Pressure in Rabbits by Telemetry," INVESTIGATIVE OPHTHALMOLOGY & VISUAL SCIENCE, Vol. 37, No. 6, pp. 966–975, May 1996. Schnell and McLaren utilized technology commercially available from Data Sciences International of St. Paul, Minn., to obtain hydrostatic IOP within the midvitreous and aqueous humor, respectively.

SUMMARY OF THE INVENTION

The present invention provides a method and apparatus for directly and continuously monitoring intraocular pressure.

The present invention concerns a device for measuring intraocular pressure (IOP) of a patient (an IOP monitoring system). The IOP monitoring system includes an in vivo sensor. The sensor includes a capacitive pressure sensor and an inductive component. An excorporal (external to the patient) instrument remotely measures the pressure in the eye, provides readout of pressure values and energizes the sensor, thereby permitting the instrument to determine the intraocular pressure.

Additionally, the present invention relates to a method for measuring intraocular pressure of a patient. A signal is generated with an instrument external to the patient for remotely energizing an in vivo sensor. Interaction between the signal produced by the instrument and the sensor is measured. The interaction is correlated with intraocular pressure.

Still other objects and advantages of the present invention will become readily apparent by those skilled in the art from the following detailed description, wherein it is shown and described in the preferred embodiments of the invention, simply by way of illustration of the best mode contemplated of carrying out the invention. As will be realized, the invention is capable of different embodiments and its several details are capable of modifications in various obvious respects, without departing from the invention. Accordingly, the drawings and description are to be regarded as illustrative in nature and not as restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENT(S)

Figure 1:
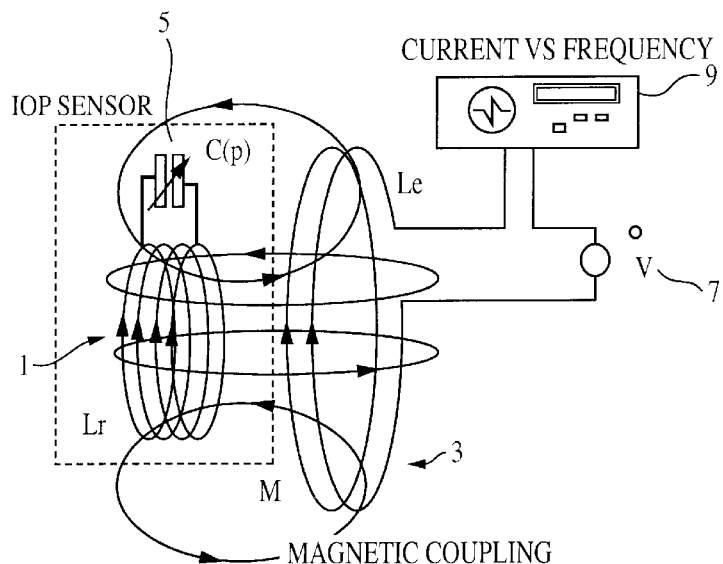
FIG. 1 represents a schematic view of an embodiment of a device according to the present invention.

The present invention greatly enhances a physician's ability to treat a patient suffering from end-stage glaucoma or other ill effects of elevated intraocular pressure by providing the physician with the capacity to continuously monitor IOP. A significant advantage of the present invention is that the patient need not visit the physician to have their intraocular pressure monitored. In fact, information concerning a patient's intraocular pressure may be delivered to a physician over data communications networks such as a telephone and an internet appliance.

A significant benefit of the present invention is that it overcomes problems and doubts concerning indirect determination of intraocular pressure. Indirect measurements are suspect at least in part because of concerns related to correlation, accuracy, and consistency in relating measurements to actual aqueous humor hydrostatic pressure.

By permitting continuous outpatient monitoring of intraocular pressure, the present invention permits physicians to promptly and accurately detect ocular hypertension, and it will enable them to select the most efficacious treatment for the patient. The present invention will also make it possible to detect occult spikes in intraocular pressure and can make a patient aware of these events so that medical attention will be sought more promptly. In summary, the present invention provides an ambulatory intraocular pressure monitoring system that represents a revolutionary approach in glaucoma research and clinical management.

The system according to the present invention includes an in vivo sensor and an instrument external to the patient for remotely energizing the sensor. The sensor includes a capacitive pressure sensor and an inductive component. The instrument remotely measures the pressure in the eye, provides readout of pressure values and energizes the sensor, thereby permitting the instrument to determine the patient's intraocular pressure. Typically, at least a portion of the sensor directly contacts the aqueous humor of the patient, thereby making the determinations of intraocular pressure direct measurements. Since the sensor is in vivo, it is available to take measurements anywhere at any time.

To facilitate its operation, the sensor according to the present invention typically does not require a power source. Such a "passive" sensor will not require maintenance with respect to replacing a power source. Also, a passive sensor does not have associated issues with respect to adverse impact of implanting a power source in or near a patient's eye. Along these lines, the present invention minimizes the chance of infection or epithelial downgrowth at the implant site. Other adverse effects could result from degradation of a power source under physiological conditions and adverse affects on the patient's eye as a result thereof.

As a passive sensor, the present invention may include an inductor in which a current is induced by the patient external instrument. The inductor may be connected to an element that provides a pressure measurement. One example of such an element is a pressure sensitive capacitor in which the capacitance varies with pressure exerted on the capacitor.

The sensor is energized by the instrument's exciter coil. To accomplish this, the instrument may include a power source and an exciter (coil) connected to the power source for supplying electric current to the exciter. Supplying power to the exciter results in energizing the sensor.

In a device according to the present invention that includes a sensor and instrument such as those described above, the sensor and instrument may be considered magnetically coupled. Along these lines, the inductor may include a coil, which may be referred to herein as a responder coil. The exciter may include an exciter coil. In such an arrangement, the sensor can be powered by a "link field" produced by the exciter that has electrical properties affected by the state of the sensor. Thus, the exciter condition is related to the pressure acting on the sensor.

FIG. 1 illustrates the magnetic coupling of the responder coil 1 and the exciter coil 3. According to physical principles, the current flowing in the exciter coil generates a magnetic field that interacts with the responder coil. The responder coil may have a fixed inductance that resonates with a separate pressure dependent capacitance. This configuration differs from certain known configurations in which a self-capacitance of a coil pair is resonated with the coil inductance and both the inductance and capacitance are varied with pressure. In the arrangement shown in FIG. 1, the exciter coil is "near-field" magnetically coupled to the responder coil of the sensor. This inductive link is noise tolerant and suited for in vivo sensor reception-transmission of energy/data.

The exciter coil and the responder coil are both resonant circuits. The exciter coil can be made to resonate over the resonant frequency range of the sensor. Changes in intraocular pressure alter the capacitance of the pressure sensitive capacitor 5, thereby altering the resonant frequency variation of the responder coil. A power source 7 and a processor 9 may be included in a circuit with the exciter.

Figure 2A:
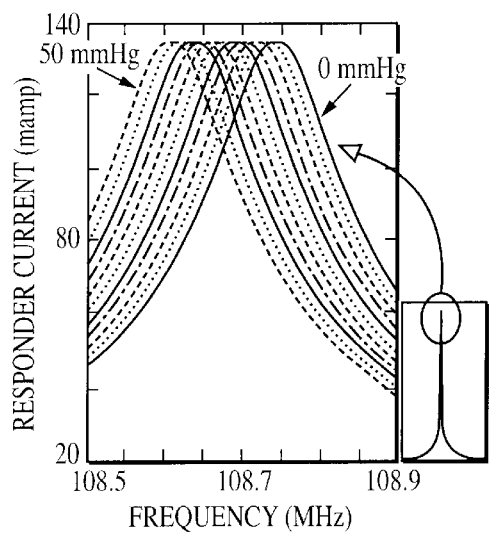
FIGS. 2a and 2b represent graphs that illustrate relationships between interacting exciter and responder coil-currents and frequency.
Figure 2B:
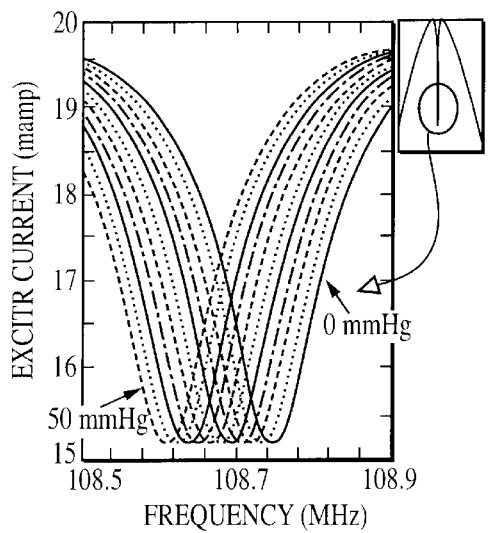

FIGS. 2a and 2b represent graphs that provide an electrical analysis of the magnetically coupled circuit shown in FIG. 1. The values shown in FIGS. 2a and 2b were produced utilizing a responder coil that included 2 turns having a diameter of about 12 mm. The exciter coil in this system included three turns having a diameter of about 60 mm. The two coils were separated by about 20 mm. The exciter coil is made to broadband resonate over the narrow-band resonant frequency range of the sensor. In the system that produced the results shown in FIGS. 2a and 2b, pressure was a parameter. The capacitor pressure sensitivity was assumed to be $dC(P)/dP = S_p = \sim 5\text{E-4pF/mmHg}$.

With an intraocular pressure sensor including two circuit elements, the responder coil and a pressure variable capacitor transducer, as the acting pressure increases there is a corresponding increase in capacitance. The coil and transducer are connected together forming what is commonly referred to as an LC-circuit. The stimulator and power source can provide repetitive frequency sweeps of electromagnetic energy to the sensor. The stimulator frequency would be swept over a sufficiently wide range to ensure that the implanted LC circuit would be induced to "ring" at its resonant frequency.

A current is induced in the sensor circuit by magnetic waves supplied by the stimulator circuit. The resonant frequency is inversely related to the intraocular pressure. In other words, the instrument includes an exciter inductive coil to magnetically near-field couple to the sensor through mutual inductance.

The resonant frequency may be determined from the Equation 1 below.

$$F_r(p) = (2\pi L \times C(p))^{-1/2} \qquad (1)$$

According to Equation 1, a pressure increase (decrease) causes the intraocular pressure sensor's resonant frequency to decrease (increase). Measuring the sensor's resonant frequency makes it possible to determine the pressure acting on the sensor.

Near the responder resonance, however, there is a significantly increased coupling to the exciter. In this case an absorption dip occurs. The nature of this dip depends on a number of factors, which can include the relative orientation of the two coils, the distance between the coils' centers, and their electrical quality factor (Q).

Figure 3:
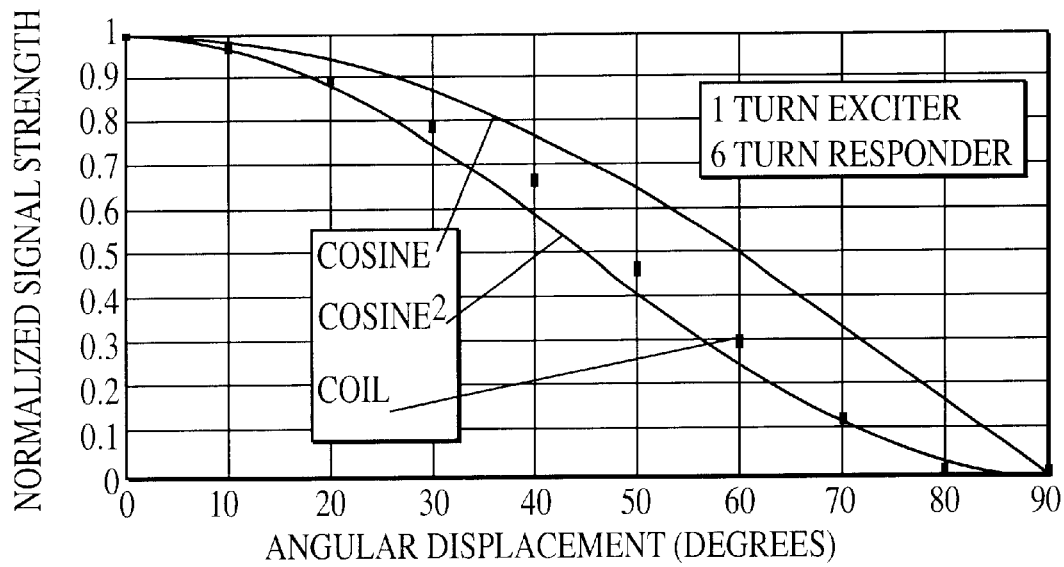
FIG. 3 represents a graph that illustrates a relationship between normalized signal strength and angular displacement.

The amount of coupling between the coils is also a function of the area through which the magnetic field passes. Maximum coupling occurs for the greatest cross-sectional area. This is an important factor that relates to the relative orientation of an IOPS and measurement unit. As the angle between coils, which is measured as the angle between the coil area vectors with the coils rotating on parallel axes, changes from 0 to 90 degrees, the depth of the dip follows a curve that lies between a cosine and cosine squared behavior, as illustrated in FIG. 3. The theoretical relationship between coil orientation and "signal strength" can be derived from these measurements.

Figure 4:
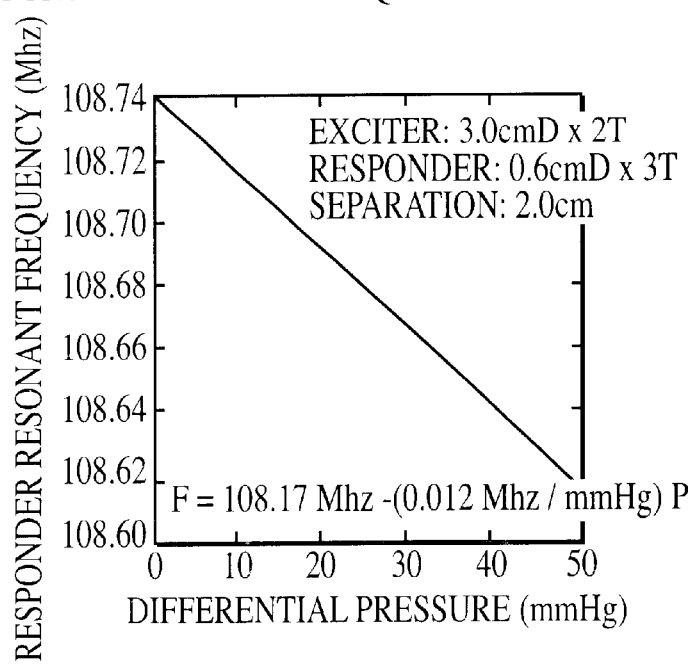
FIG. 4 represents a graph that illustrates a relationship between IOP sensor pressure versus resonant frequency for $S_P=\sim 5E\text{-}4pF/mmHg$.

FIG. 4 represents a graph that illustrates a predicted relationship between pressure and resonant frequency derived for the coil configuration utilized to produce the results shown in FIGS. 2a and 2b. Therefore, FIG. 4 indicates the sensor resonant-frequency shift that would be expected as a function of intraocular pressure. This frequency variation is measured, and may be related to the sensor intraocular pressure, as described in greater detail below.

Figure 5:
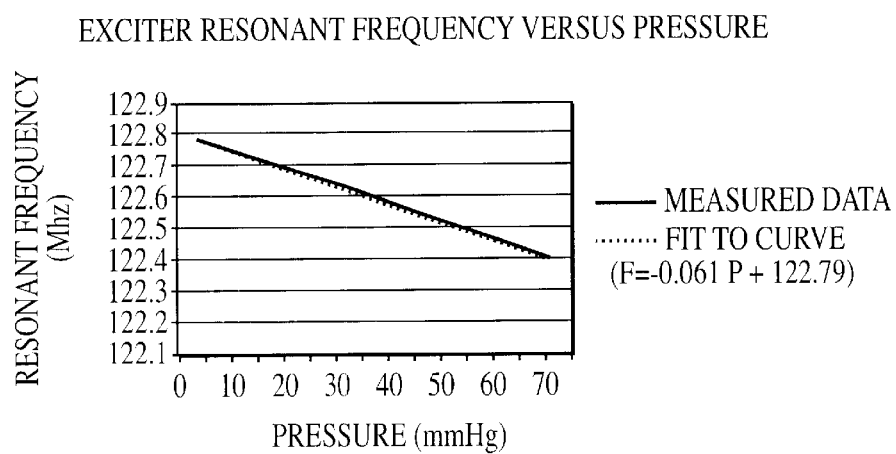
FIG. 5 represents a graph that illustrates a relationship between measured pressure and frequency.

FIG. 5 represents an experimentally determined graph that illustrates the relationship between pressure and resonant frequency utilizing data experimentally obtained from a laboratory apparatus. FIG. 5 also illustrates a curve fit to the experimental data. In comparing FIGS. 4 and 5, it can be seen that FIG. 5 confirms the operation and accuracy of the device according to the present invention.

As described above, the magnetically coupled sensor and instrument may each include a coil. The composition of the material making up the sensor and instrument coils as well as the design of each of the coils may vary. With respect to the design, the number of turns making up the coils, the diameter of the coils, the thickness of the material making up the coils, the separation of each turn, and other parameters may vary. Additionally, the orientation of the coils with respect to each other may also vary.

Figure 6A:
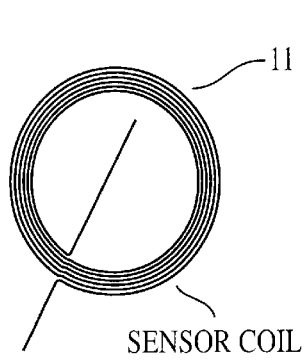
FIG. 6a represents a top view of an embodiment of an inductor coil that may be included in an inductive component according to the present invention.
Figure 6B:
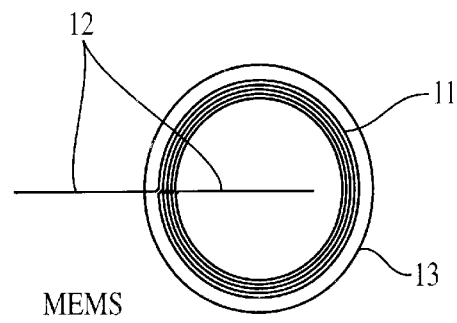
FIG. 6b is a view of an embodiment of a micro electro-mechanical systems (MEMS) coil that may be included in a device according to the present invention.

FIGS. 6a and 6b illustrate an embodiment of a sensor coil according to the present invention. The sensor coil 11 shown in FIGS. 6a and 6b includes five turns with leads 12 extending in opposite directions therefrom. FIG. 6 shows the coil and a Molteno implant 13 that the coil is arranged within. Although the coil is shown in association with a Molteno implant, any known, approved and accepted glaucoma pressure-reducing fluid shunts (GPRFS), such as Molteno, Krupin, or Ahmed devices, as well as any associated surgical practice may be utilized. According to another embodiment, the coil includes 9 turns.

Each end of the coil terminates in a lead having a length of about 3 mm. The coil has an outer diameter of about 4.55 mm and an inner diameter of about 3.75 mm. The width of the material making up to coil is about 0.05 mm. Each turn of the coil is separated from adjacent turns by about 0.05 mm. The sensor coil may or may not be planar.

Of course, the dimensions of the coil may vary. This coil's size can be scaled up or down in diameter up to a factor of 5×. Along these lines, the number of turns in the sensor coil may be from 1 to more than 50.

The materials making up the sensor and instrument coils may vary. Examples of materials include 36 AWG (125 µm D) copper wire, copper foil, copper-beryllium foil, copper-plated beryllium-copper, aluminum, gold, and other materials.

With some applications, certain materials may provide better performance. This is demonstrated by the results represented in the graph shown in FIG. 7, which illustrates relationships between the log of the magnitude of $s_{11}$ and breadboard frequency and frequency in a coil according to the present invention. $S_{11}$ is known as the input microwave scattering parameter of the IOP resonant sensor circuit. It is roughly a measure of the power that is absorbed by the circuit when fed by a generator.

Figure 7:
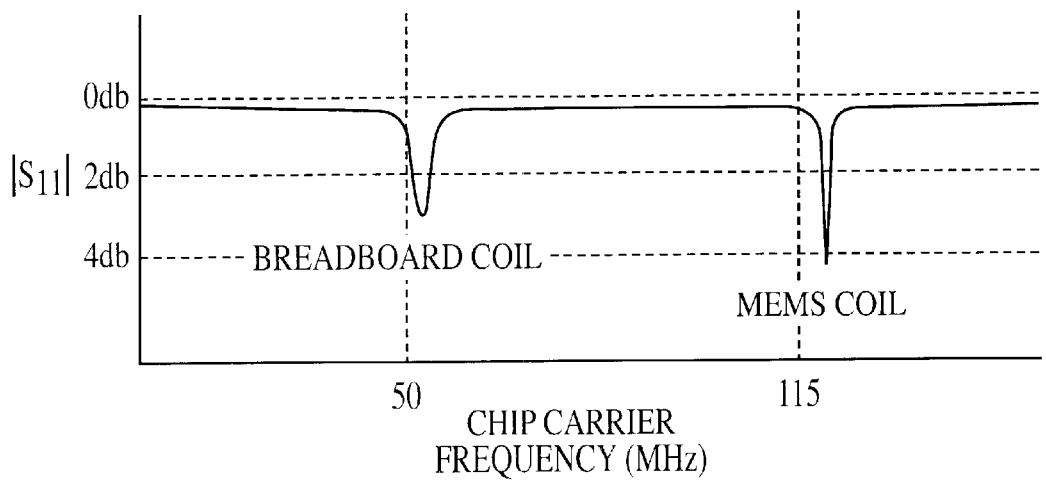
FIG. 7 represents a graph that illustrates relationships between the log of the magnitude of $s_{11}$ and breadboard frequency and frequency in a coil according to the present invention.

The graph shown in FIG. 7 illustrates results obtained with two responder coils, one flat-wound coil made with five-turns of 36 AWG (125 μm D) copper wire and the other a flat coil, micro electromechanical systems (MEMS) fabricated copper-plated beryllium-copper inductor (five 75 μm T×125 μm W turns). The coupling angle and spacing are the same for both coils. The deeper dip of the Cu plated beryllium-copper coil is due to a higher Q inductor.

With respect to the present invention, in the graph shown in FIG. 7, the "dips" that appear at particular frequencies indicate the resonant frequencies and qualities of the two forms of coil, breadboard or hand-wound wire and MEMS fabricated coil. The sharper and deeper the dip the better the quality. This demonstrates that the MEMS coil is superior to the breadboard coil.

Microsystem Technology or MEMS Technology is the integration of miniaturized components of sensor applications using newly developed miniaturization techniques. Microsystems combine microelectronic components (Integrated Circuits) with micromechanical or micro-optical components. The microelectronic element employs standard semiconductor technology to analyze and manage the output data of the micromechanical or optical element. Microsystem Technology is strategically important to many industries and applications. Microsystems offer the possibility to miniaturize and integrate sensors, provide more intelligent sensing electronics and electronic controls, and enhance key elements found in many applications.

Microsystem technologies can be found in manufacturing, automotive, aircraft, security, environmental, construction, medical, and communication applications. Important branches of industry that will profit from further development in microsystem technology include electronics, chemical, precision manufacturing, optical, and food processing industries. Just as microelectronic components are found in almost every electronic device, microsystems using micromechanical components will be as pervasive and essential in the future.

The manufacturing of the electronic portion of microsystems is well understood and can be done in the same manner as traditional semiconductor production. However, the 3D-micromechanical elements are sufficiently different from mainstream semiconductor devices to require new process steps, such as wafer bonding, and manufacturing equipment, although still capable of mass quantity production.

MEMS technology is applicable to a variety of fields. One of the first microsystem applications, the pressure sensor, uses the combination of mechanical sensing elements and electronic circuitry. The micromechanical components are produced on silicon wafers, a material well known in chip manufacturing. Consequently, it is possible to process both mechanical and electronic elements on the same silicon substrate. In addition to the extraordinary mechanical and electrical properties, silicon also provides exceptional chemical properties. The three dimensional silicon microsystems with its multifaceted electrical, mechanical, and chemical properties have a variety of application possibilities, including miniaturized pressure and acceleration sensors used in the automobile for airbags, in-situ tire pressure gauges, emission measurements, and engine control. Additionally, MEMS technology could be utilized ink jet heads with capillaries and micro valves that meter the application of ink on paper in increments of one thousandth of a millimeter. Also, MEMS technology makes it possible to produce pumps and motors the size of a fly's head for metering chemicals. DNA analysis that performs millions of simultaneous process steps could be carried out utilizing MEMS technology. Furthermore, MEMS technology could be used in micro lenses and micro switches with diameters smaller than a human hair used in fiber optic circuits for communication and lightning fast Pcs.

Similar to the design of the coils, the fabrication of the coils may be accomplished in a variety of ways. The following discussion applies to both the exciter and responder coils. In the event that the coil is a MEMS coil, the coil may be fabricated as follows. A layer of an electrically conducting material is provided on a substrate. The layer of electrically conducting material is coated with photoresist. Next, the photoresist is exposed and developed to expose portions of the layer of electrically conducting material. Then, the exposed portions of the layer of electrically conducting material are etched. The photoresist is stripped. Subsequently, the substrate and remaining portions of the layer of electrically conducting material are separated.

According to a particular embodiment, two and three mil beryllium copper foil may be waxed down to an aluminum substrate. The beryllium copper foil may then be coated with negative acting, dry-film photoresist. The photoresist-coated beryllium copper foil was then patterned using a processed photoplot of the artwork. After exposure and development, the beryllium copper foil was spray etched using a ferric chloride solution. After etching, the remaining photoresist was stripped from the coils. The substrate with the etched coils was placed in acetone, which dissolved the wax holding the coils to the aluminum substrate. Another coil configuration would have microelectronic circuit processing applied to make miniature coils on a substrate surface. A coil also can be fabricated using precision winding techniques for making wire-wound coils.

Figure 8:
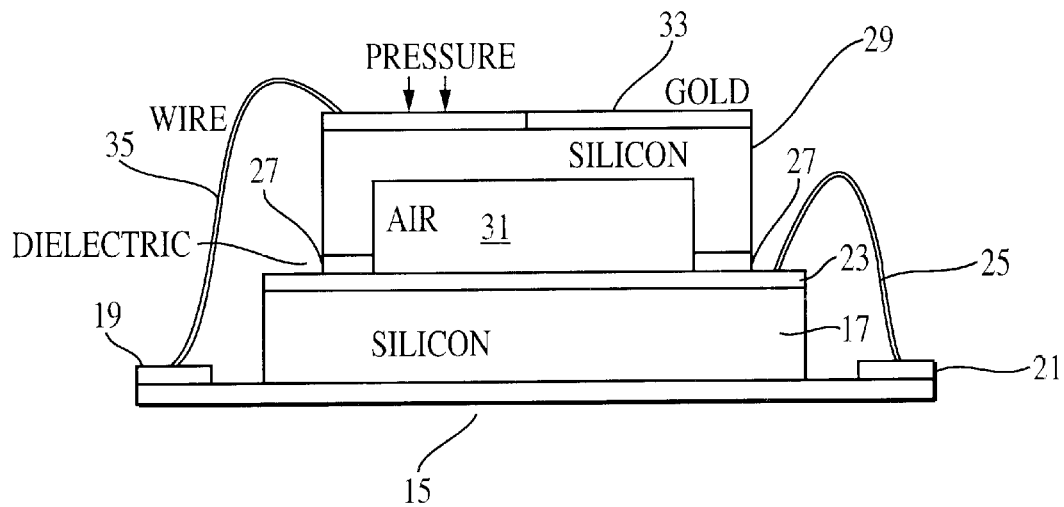
FIG. 8 represents a cross-sectional view of an embodiment of a pressure sensitive capacitor according to the present invention.

As with the design and fabrication of the coils, the capacitor may have different designs and methods for making them. FIG. 8 illustrates a cross-section of one embodiment of a capacitor according to the present invention. The embodiment illustrated in FIG. 8 is a MEMS silicon diaphragm capacitor pressure sensor. A similar device is described by Kevin, H. et al., *A VERSATILE POLYSILICON DIAPHRAGM PRESSURE SENSOR CHIP, IDEM* 91, pp. 761–764, 1991, the entire contents of which are hereby incorporated by reference. The capacitor includes a chip carrier 15 on which a region of silicon 17 and contacts 19 and 21 sit. A layer of electrically conducting material 23 is arranged on silicon layer 17. Lead 25 connects electrically conducting layer 23 to contact 21. Regions of dielectric material 27 are arranged on portions of electrically conducting region 23. A region of silicon 29 contacts the dielectric regions 21, leaving an air gap 31 between the silicon region 29 and the electrically conducting region 23. A layer of electrically conducting material 33 is arranged on the silicon region 29. Any electrically conducting material may be utilized. In the embodiment shown in FIG. 8, the electrically conducting material 33 is gold. A lead 35 connects contact 19 with electrically conducting layer 33.

The capacitor shown in FIG. 8 would be attached to the leads of the responder coil shown in FIGS. 6a and 6b.

A variety of methods may be utilized to make the pressure sensitive capacitor depending at least in part upon the design of the capacitor. These include using available integrated circuit or MEMS fabricating technology.

The sensor, including the responder coil and the pressure sensitive capacitor may be enclosed and/or encapsulated suitable for implantation into a patient. The enclosure and encapsulation materials are biocompatible. To facilitate the functioning of the present invention, the enclosure provides a connection between the pressure sensitive capacitor and the patient's aqueous humor. This direct connection in part is responsible for the tremendous benefits achieved according to the present invention.

Figure 10A:
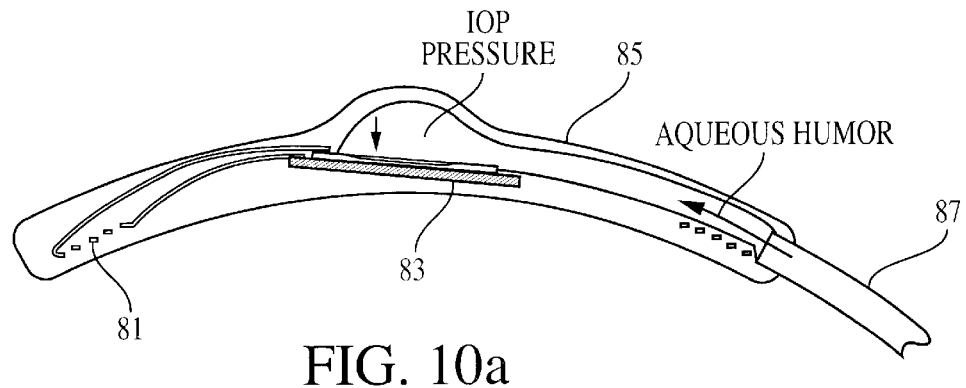
FIG. 10a represents a cross-sectional view of an embodiment of a device according to the present invention.

The enclosure or "packaging" of the sensor may vary, depending upon the particular application. Two examples of packaging configuration are shown in FIGS. 10a and 10b. A first example (FIG. 10a) of a sensor is self-contained and applicable to ambulatory animal/human subjects. It records a continuous record of intraocular pressure unmodified by pressure reducing loss of anterior chamber fluid. Such data can be very important for medical research pertaining to the etiology of ocular diseases and conditions caused by or causing abnormal intraocular pressure (IOP), such as glaucoma diseases and conditions. Such data has been unavailable in the past, advancing both treatment and medical knowledge.

A second example of sensor (FIG. 10b) may be utilized with keratoprostheses. This device can be configured to enable an ophthalmologist to measure IOP with a remote sensing hand held interrogator. Because glaucoma is a frequent complication, this sensor may be incorporated into a glaucoma pressure-reducing fluid shunt implanted with a keratoprosthesis. Any known, approved and accepted glaucoma pressure-reducing fluid shunts (GPRFS), such as Molteno, Krupin, or Ahmed devices, as well as any associated surgical practice may be utilized. In general, a sensor of the second type described above could be incorporated in one or more types of GPRFS used in the treatment of advanced stages of glaucoma. The present invention permits both physician and patient to conveniently and remotely monitor IOP during treatment, from hospital, home, or any other location.

The examples of sensor "packaging" described above typically only involve changes in the housing that encloses the sensor. Actually, both settings are ambulatory, may utilize the same sensor and instrument to determine intraocular pressure. Additionally, both examples of "packaging" include biocompatible housings as described in greater detail herein.

The first example of a sensor can incorporate micro electromechanical systems (MEMS) components that can include a miniature inductor and pressure sensitive capacitor. An external data acquisition module, such as the instrument described herein, may be included with the first type of sensor for remotely interrogating the intraocular pressure sensor and recording pressure measurements for immediate or subsequent read out by a local or remote computer using application specific software, via wireless link, a modem, or via the internet, for example. Accordingly, the device may include a memory for storing the measurements.

The first example of a sensor directly and continuously measures unmodified intraocular pressure of the aqueous humor; the second example of a sensor obtains measurements of modified pressure during the treatment of elevated intraocular pressure. This second type of sensor would be measuring modified pressure.

In some cases, devices according to the present invention will provide accurate IOP data that may not be obtainable in other ways. For example, a device according to the present invention may be utilized when keratoprostheses do not respond to various tonometer methods.

Figure 9A:
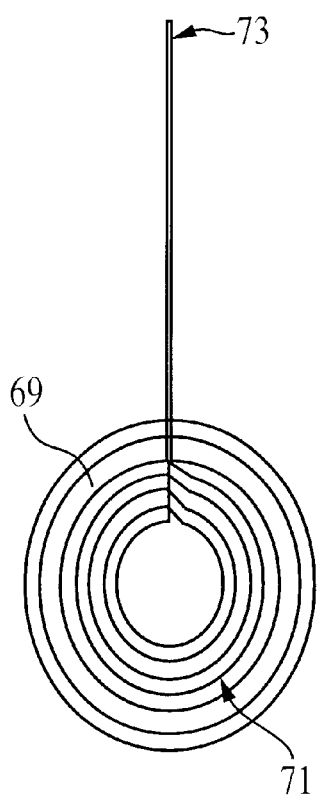
FIGS. 9a and 9b represent, respectively, overhead and side views of a Molteno shunt in which an embodiment of a sensor according to the present invention is embedded.
Figure 9B:
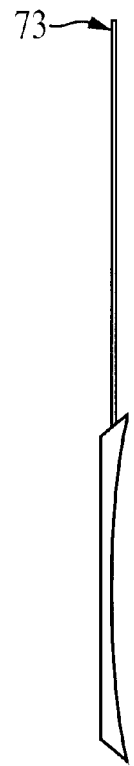

FIGS. 9a and 9b represent overhead and side views of a Molteno shunt in which a sensor according to the present invention is embedded. The sensor 69 includes a responder coil 71 and a pressure sensor 73 incorporated therein.

FIGS. 10a and 10b illustrate in greater detail devices according to the present invention incorporated into two different types of implants. Along these lines, FIGS. 10a and 10b, respectively, illustrate an example of each of the two above-described types of implementations of a sensor according to the present invention. In FIG. 10a, the sensor, including the coil 81 and capacitor 83, is incorporated into an implant 85 made of biocompatible material. A shunt or stent 87 extends from the body of the implant. Typically, the shunt leads to the anterior chamber of the patient's eye. The diameter of the shunt can vary. According to one embodiment, the shunt tube has a 20–30 mil inside diameter. The shunt provides a connection to deliver the aqueous humor into the interior of the implant where the sensor is located. As described above, the implant of this first example of a sensor does not provide means for relieving pressure. Therefore, the implant shown in FIG. 10a should provide an accurate measurement of unmodified patient IOP.

Typically, the implant is just large enough to accommodate the responder coil. The implant shown in FIG. 10a has an outer diameter of about 0.5 inch. At its widest, the pressure sensitive capacitor has a diameter of about 0.15 inch.

Unlike the implant shown in FIG. 10a, the implant 89 shown in FIG. 10b includes a pressure release function in this case in the form of a pressure release surface 91. The aqueous humor is delivered to the implant through shunt 90. Both embodiments are implanted under the conjunctiva of the patient's eye. However, only FIG. 10b illustrates the conjunctiva 93. The pressure sensor is attached to the external sclera of the patient's eye and protrudes into the anterior chamber via sclera penetration posterior to the limbus. A miniature pressure-sensitive capacitor is thus immersed in the aqueous humor supplied from the anterior chamber. The IOP is applied to the capacitor as indicated by arrows 95. Arrows 97 indicate the pressure release by diffusive transfer to the surrounding body space.

Figure 10C:
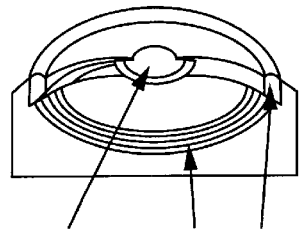
FIG. 10c represents a perspective view of a portion of a patient's eyeball with the embodiment of a device according to the present invention implanted under the conjunctiva.
Figure 10B:
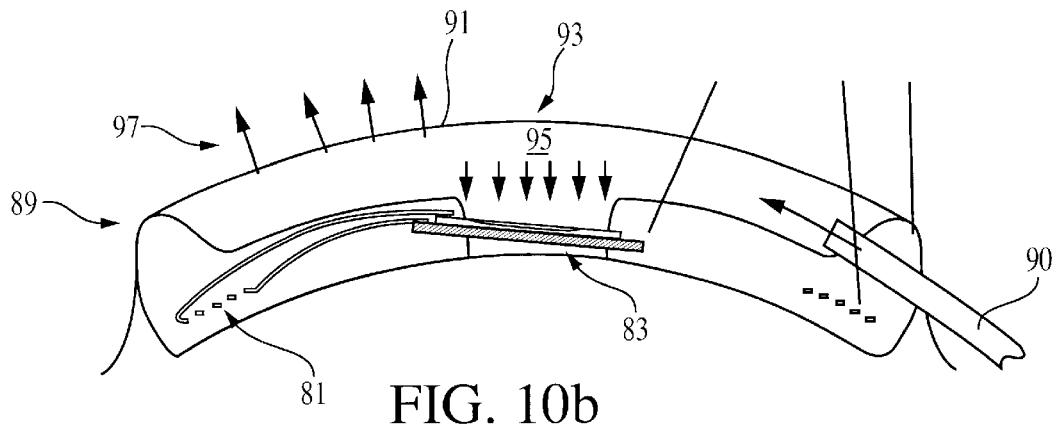
FIG. 10b represents a cross-sectional view of another embodiment of a device according to the present invention.

FIG. 10c provides a perspective view of the embodiment shown in FIG. 10b implanted in a patient. Similarly, FIG. 10e illustrates a sensor 111 according to the present invention arranged in a Molteno implant disk. 109

Figures 10D, 10E:
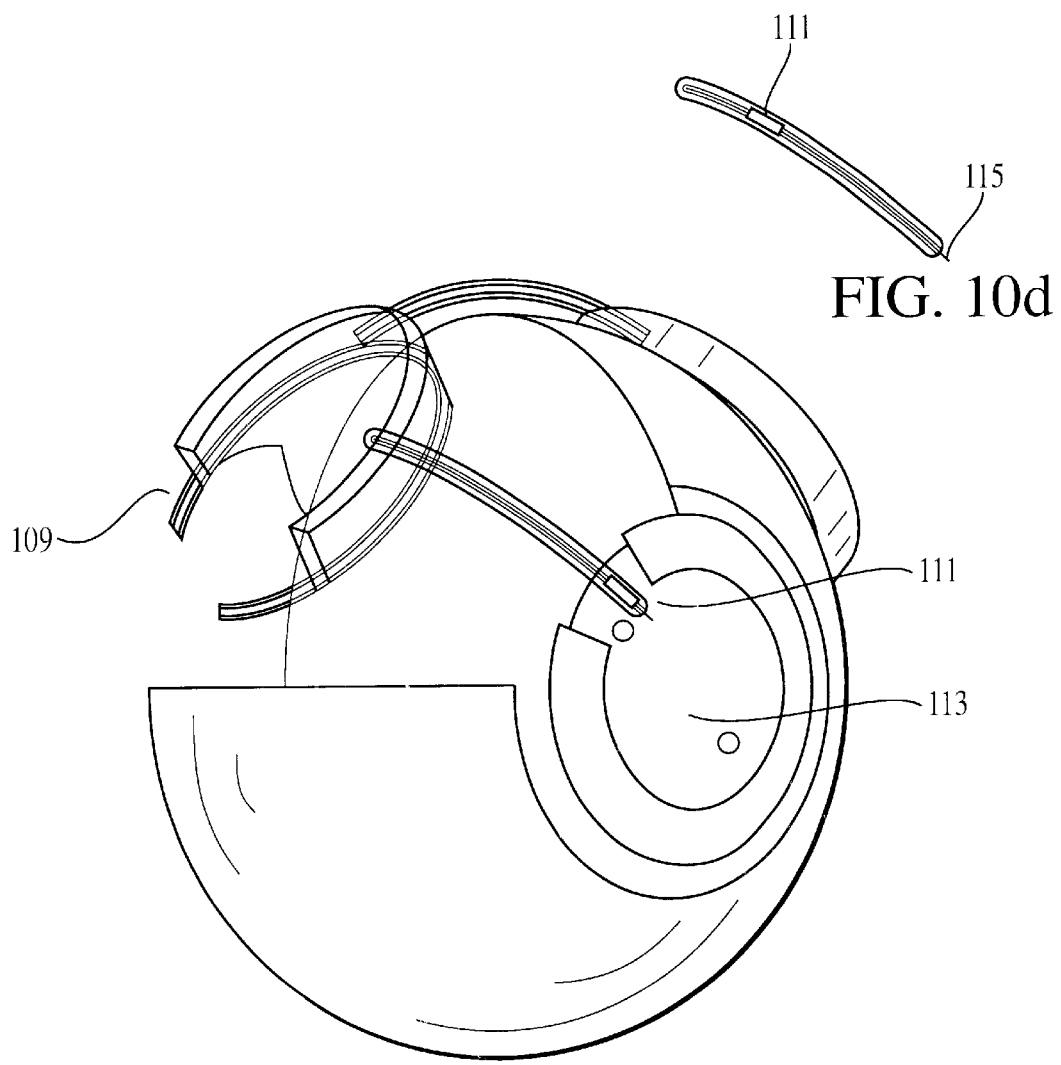
FIG. 10d represents a perspective view in which a capacitive sensor component is in a retracted position in the Molteno shunt tube.
FIG. 10e represents a perspective view of a completed Molteno process device showing an embedded IOP sensor with the capacitive sensor component placed at the distal end of the shunt tube.

In FIG. 10d the capacitive MEMS sensor 111 component is in a retracted position so as not to interfere with the surgical placement and trimming of the shunt tube. This tube once positioned is then cut to length as required. Following this trimming procedure a "thread" 115 attached to the sensor is pulled, using a suitable surgical instrument, thereby bringing the MEMS sensor to 111 a location near the end of the tube. Any excess thread length is cut and removed.

Figure 11:
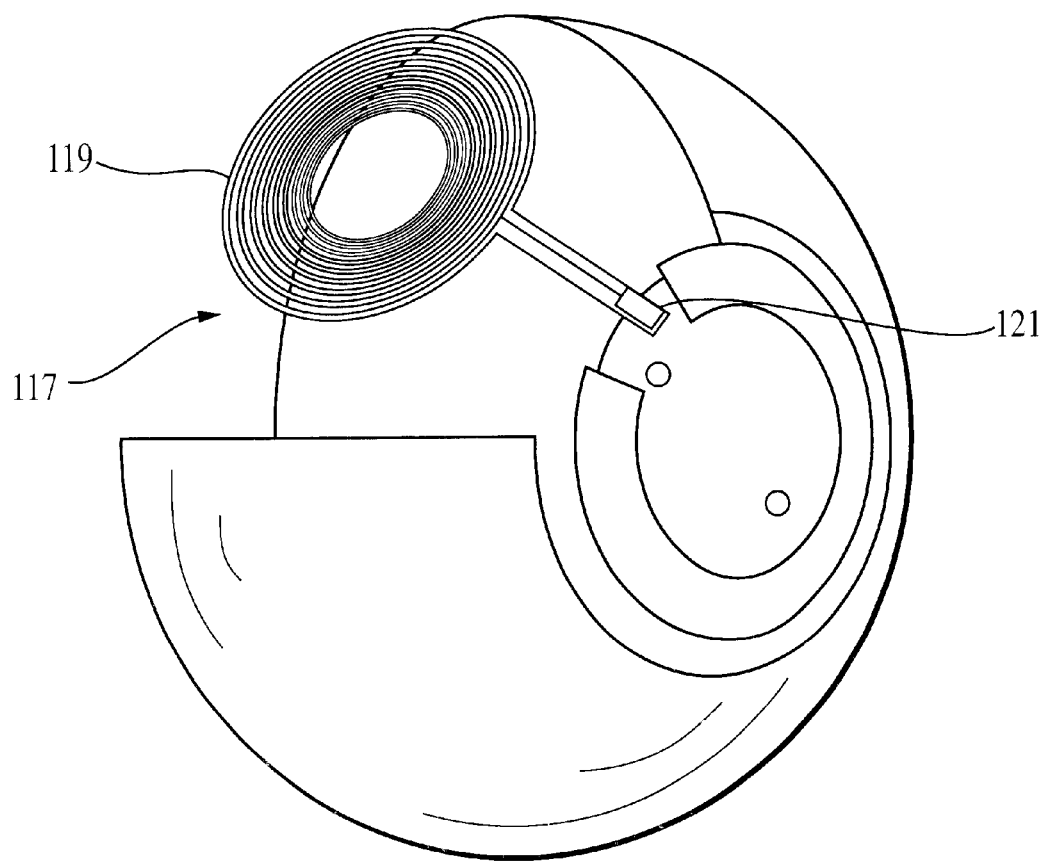
FIG. 11 represents an alternate embodiment of the IOP sensor.

FIG. 11 illustrates a stand-alone device 117 that has been encapsulated with a biocompatible material. In the embodiment shown in FIG. 11, all of the device, including the responder inductor coil 119, has been encapsulated except for the capacitor 121 so that the aqueous humor can act directly on the capacitor.

Other forms of the sensor can include a membrane type that can be placed on various locations of the eye globe including about the cornea. Of course, these represent just a few examples of possible implementations of the present invention. Additionally, with the advent of the newer micro-robot technology, implantable aqueous "pumps" could be developed which could be incorporated into a feedback system that automatically regulates intraocular pressure.

Figure 12:
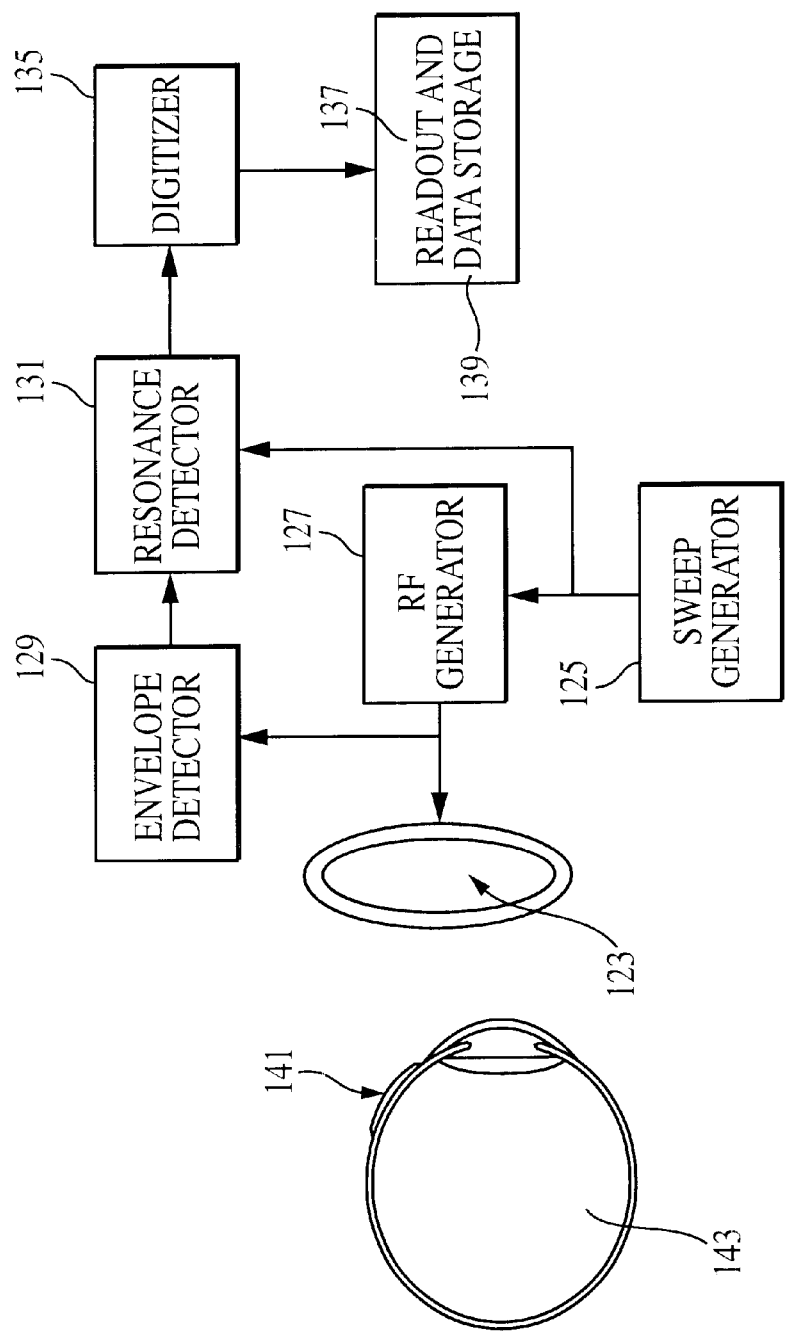
FIG. 12 is a block diagram that illustrates operation of a device according to the present invention.

Unlike the sensor according to the present invention, the instrument is external to the patient. No wired connection is made between the sensor and the instrument. This is what is meant by remote when referring to the energizing of the sensor, for example. FIG. 12 shows elements that may be included in an instrument. These elements include, among others, an exciter coil 123, a sweep generator 125, an RF generator 127, an envelop detector 129, a resonance detector 131, a digitizer 135, a display or readout 137, and data storage 139. The responder coil 141 has been implanted in the eye 143.

As described above, the instrument exciter coil may be magnetically coupled to the sensor. The exciter coil may include any number of turns necessary to permit the exciter to function in energizing the sensor and then determine the intraocular pressure based upon interaction with the sensor. The coil is connected to a power source, as is illustrated in FIG. 1.

Figure 13:
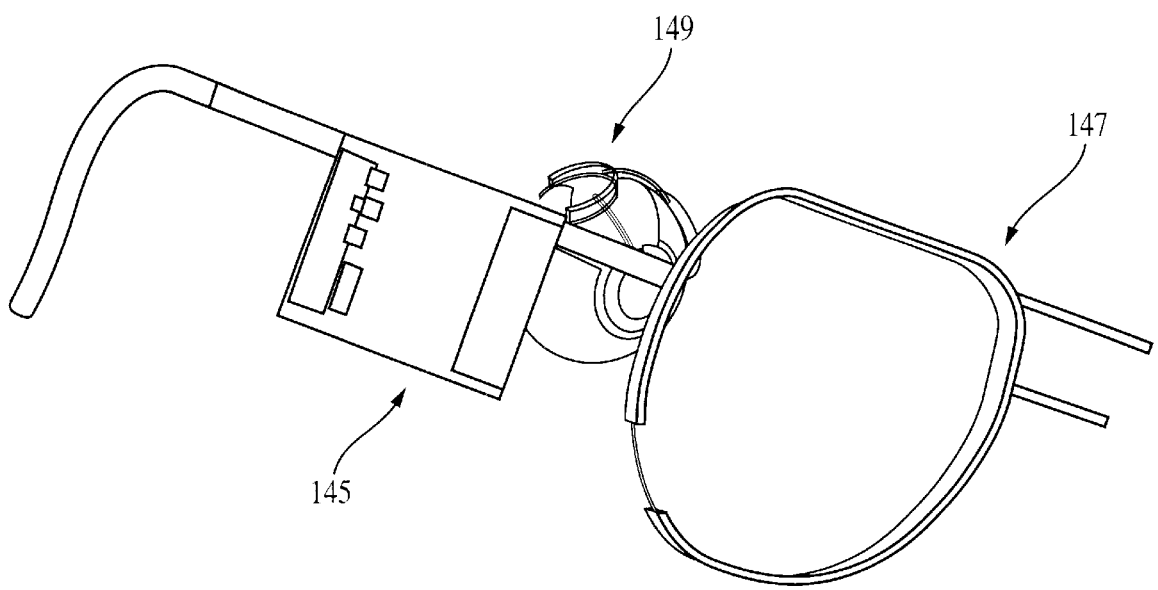
FIG. 13 represents a perspective view of an embodiment of a pair of spectacles including an embodiment of an instrument attached to the spectacles.

The instrument can be worn by the patient, for example, attached to or incorporated in spectacles worn by a patient. FIG. 13 shows an embodiment that includes an instrument 145 attached to a pair of spectacles 147. The instrument could also be incorporated into the temple of the spectacles. Any other arrangement could be utilized as long as it permits the instrument to be located a distance from and in an orientation with respect to the sensor 149 that permits the device to function properly. Typically, the instrument is arranged about 1 cm to about 2.5 cm away from the sensor.

In addition to the exciter coil and power supply, the instrument could include a memory device for displaying and/or recording results of energizing of the sensor. The memory could include any commonly available memory, such as any solid-state memory device, for example any random access memory (RAM), which could potentially store millions of measurements, using currently available memory technology. The results of the energizing of the sensor could be converted to corresponding values for intraocular pressure, which could then be stored in the memory.

Furthermore, the instrument may include a processor for carrying out one or more tasks. The tasks that a processor could carry out can include controlling the energizing of the instrument. This may include controlling delivery of power to the exciter coil. Details of the carrying out of the excitation are described below. The processor may also or alternatively translate the results of energizing of the sensor into values of intraocular pressure. Additionally, the processor or other circuitry could convert measurements of IOP into a digital format, which may be stored in the memory.

In addition to or in place of a processor located in the instrument, the device could include a processor remote from the instrument. In such embodiments, one or more of the functions performed by the processor in the instrument could be performed by the remote processor.

In addition to the above, utilizing miniaturized circuitry, a data logger including the memory, processor and/or other circuitry could be built into the spectacle's frame. The data logger could also have the ability to download the stored data into an office-based computer for further processing.

To permit a patient and/or physician to act in cases where intraocular pressure deviates from a certain value or range of values, the instrument may include an indicator. Typically, the indicator indicates when pressure exceeds a stored threshold value. Any type of indicator may be utilized. Along these lines, the indicator may be visual, audible, tactile, and/or otherwise. For example, the indicator may include one or more lights incorporated into the instrument. Alternatively, the indicator may generate sound to signify the intraocular pressure differs from a predetermined value or range of values. Also, the indicator may vibrate. Some embodiments of the indicator may include a wireless connection that signals a caregiver that the pressure differs from the predetermined value or range of values.

Figure 14:
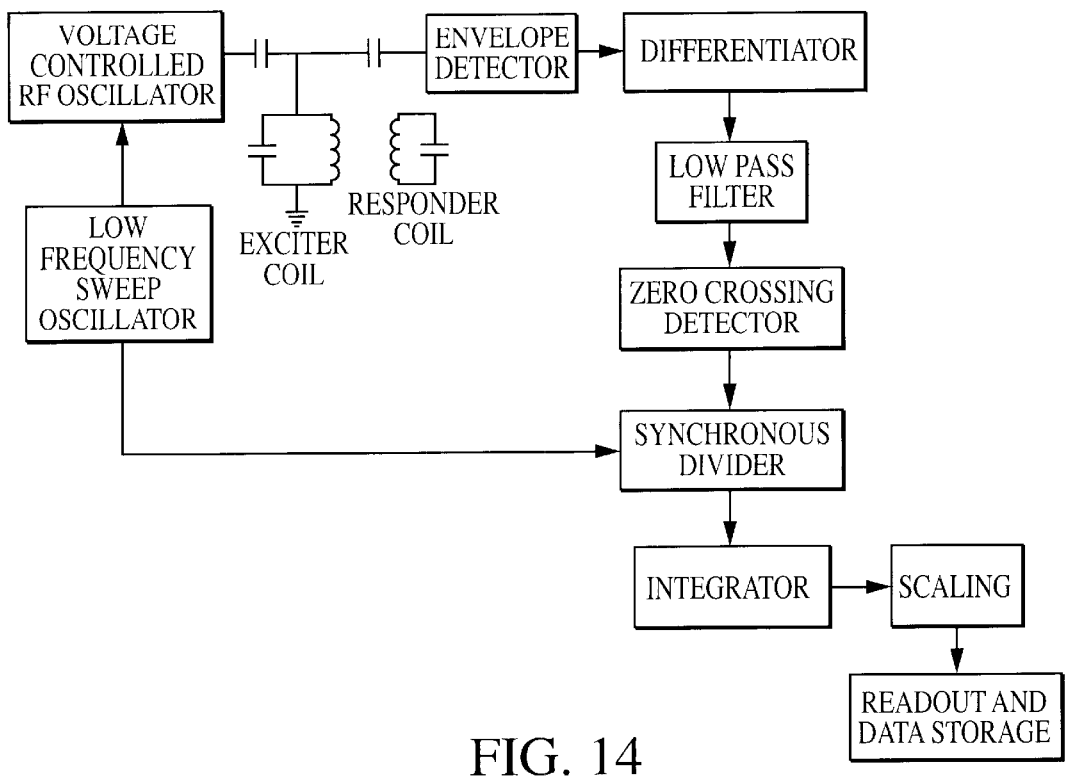
FIG. 14 represents a functional block diagram that illustrates an embodiment of a signal-processing scheme according to the present invention.

To function as described above, the instrument typically includes circuitry for detecting and processing signals related to the interaction between the exciter coil and the sensor coil and pressure sensitive capacitor. With respect to signal processing and circuit design for the measurement of pressure via the resonant dip affect described above, FIG. 14 provides a block diagram of a system that outputs a voltage proportional to the pressure "seen" by the system.

Figure 15:
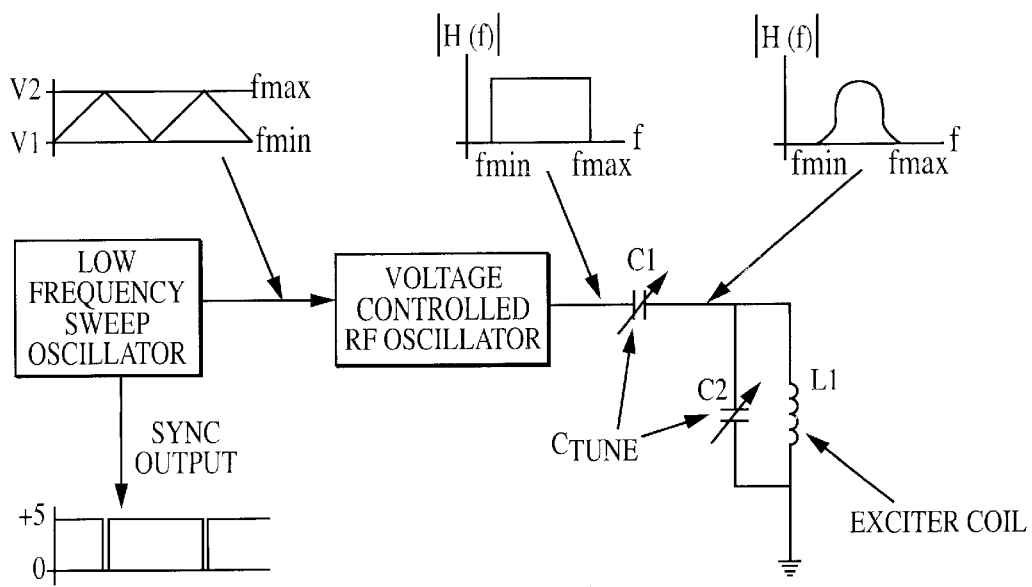
FIG. 15 represents a diagram that illustrates an embodiment of an exciter circuit according to the present invention.

FIG. 15 illustrates an example of an exciter system. In the system shown in FIG. 15, a low frequency, such as on the order of about 250 Hz, oscillator (LFO) generates a triangle wave output. This triangle wave modulates a radio frequency voltage controlled oscillator (VCO). In the system shown in FIG. 15, the VCO nominal output frequency, on the order of about 100 Mhz, is swept back and forth between the VCO minimum and maximum frequencies at the 250 Hz rate of the LFO. The VCO amplitude is fairly constant over the narrow sweep range of about 1 MHz.

Figure 16:
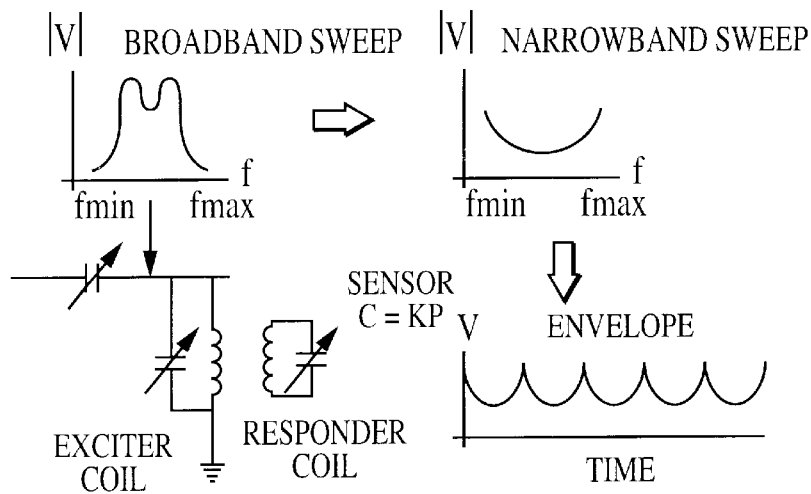
FIG. 16 represents a diagram that illustrates a narrow band detection of an exciter current/voltage.

The exciter circuit is tuned to broadband resonate at the same frequency as the responder circuit. As described above, at this point a dip occurs in the current amplitude of the exciter coil at the resonant frequency of the responder circuit. Since the frequency of the dip minimum is of primary interest, the VCO sweep range is typically set to cover a range in the vicinity of the dip minimum for the maximum frequency variation expected for the pressure range being measured. As a function of time, the frequency sweep may be repeated at the frequency of the LFO. An envelope detector may produce a dc-voltage proportional to the peak-to-peak amplitude of the RF signal across the exciter coil. Thus, in this case, the output of the envelope detector will look like the signals shown in FIG. 16.

The lowest point of the dip, the minimum, corresponds to the resonant frequency of the responder circuit. The dip will be in the middle of the sweep interval at ambient pressure and will move to the left, toward $f_{min}$, as the pressure increases. Thus, the location of the dip in the sweep interval will be an indication of the pressure seen by the responder circuit.

Trying to measure the frequency where the dip occurs during the sweep interval can be difficult so an alternate approach may also be utilized. This approach is based on the duty cycle of the sweep interval. The duty cycle is the ratio of the time from the dip to the end of the sweep interval to the total time of the sweep interval. Thus, at ambient pressure, the dip is in the middle of the sweep interval and the duty cycle is therefore 50%. As the pressure increases and the dip moves toward $f_{min}$, the duty cycle may increase. Thus, the signal processing path shown in FIG. 13 converts the envelope detector's output into a signal whose duty cycle is proportional to pressure.

Figure 17:
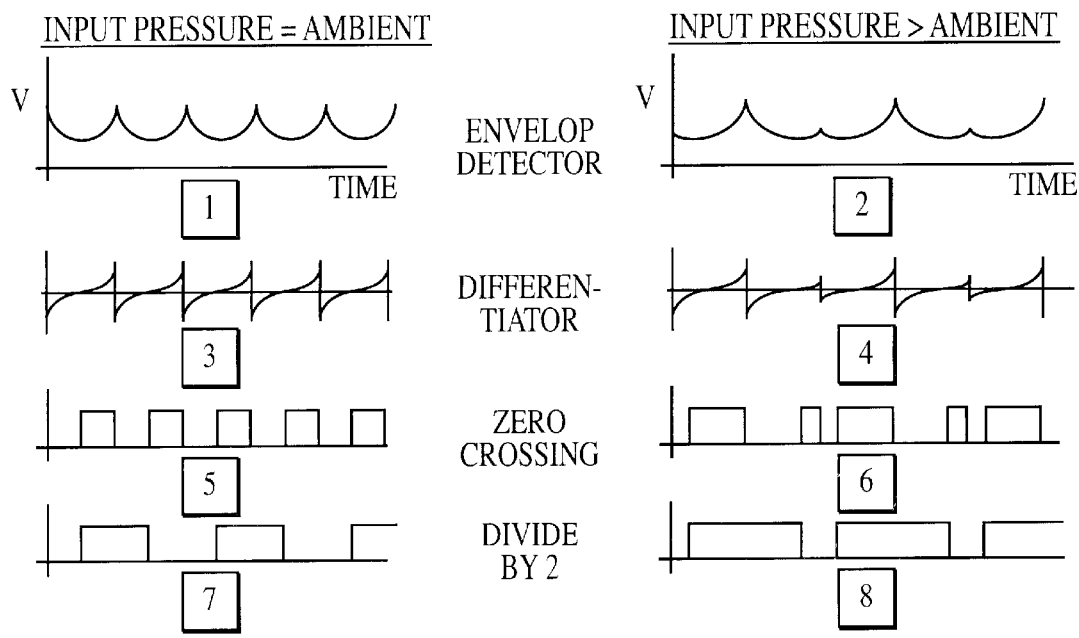
FIG. 17 represents a series of graphs that illustrate relationships between voltage and time showing a signal processing approach for intraocular pressure measurement.

FIG. 17 illustrates signal waveforms at various points in the signal processing path for both ambient pressure, i.e. graphs 1, 3, 5 and 7, and at a pressure greater than ambient, i.e. graphs 2, 4, 6 and 8. Graphs 1 and 2 illustrate the output of the envelop detector, graphs 3 and 4 illustrate the output of the differentiator, graphs 5 and 6 illustrate the output of the zero crossing detector and graphs 7 and 8 illustrate the output of the synchronous divide by 2. In all of the graphs, the vertical axis is voltage and the horizontal axis is time. The output of the differentiator, shown in graphs 3 and 4, is a measure of the slope of the output of the envelope detector signal, shown graphs 1 and 2. When the slope of the envelope detector signal is negative the output of the differentiator a will be a negative voltage, i.e. below ground or zero volts. When the slope of the envelope detector signal is positive the output of the differentiator will be a positive voltage, i.e. above ground or zero volts. When the slope is zero, i.e. at the bottom of the dip, the output of the differentiator is zero volts. The zero crossing detector output, i.e. graphs 5 and 6, simply indicates if the differentiator output is above or below zero volts. In theory, every time the differentiator signal crosses zero volts, the output of the zero crossing detector changes value. When the differentiator output signal is below zero volts the output of the zero crossing detector is zero volts and when the output of the differentiator is above ground the zero crossing detector output is +V, typically +5 volts.

At ambient pressure the output of the zero crossing detector is a symmetrical waveform with 50% duty cycle, i.e. graph 5. However, at pressures greater than ambient, the zero crossing detector output signal, illustrated in graph 6, is not symmetrical and its duty cycle has not actually changed significantly. Dividing the zero crossing detector output signal by 2, i.e. graphs 7 and 8, results in a signal whose duty cycle is again 50% at ambient pressure, i.e. graph 7, and significantly greater than 50%, i.e. graph 8, at a pressure greater than ambient. A simple integrator then converts the output of the divider into a voltage. This final voltage is now directly proportional to the pressure seen by the responder circuit. This approach simplifies the data acquisition to one of measuring a dc voltage instead of a frequency.

Analysis and characterization of the exciter-responder link can take into account variations in physical, environmental, electrical and orientation properties. For example, the device according to the present invention can take into account barometric pressure and provide a record of this influence. The data may be recorded and/or output as it is sensed and corrected for barometric pressure. Also, ambient temperature is also a factor that may be correct for and could be taken into account by temperature specific calibration tables. For animal/human intraocular pressure measurement, the subject's nominal temperature may be input to the device. The temperature compensation could be automatic and in real-time.

Automatic temperature compensation may be accomplished with the addition of a thermocouple attached to the patients skin near the eye. The signal from the thermocouple would be processed to provide an offset correction signal, much the same way the local barometer corrects for local ambient pressure effects.

Sensor calibration may be carried out utilizing an apparatus that applies known hydrostatic pressure to an in vitro sensor. Each unit's calibration table may be loaded into memory in the intraocular pressure monitor and used to "linearize" response. Sensor calibration is well known to those skilled in the art.

The present invention also includes a method for measuring intraocular pressure of a patient. According to the method, a signal is generated with an instrument external to a patient to energize an in vivo sensor that is affected by intraocular pressure. An interaction between the signal produced by the instrument and the sensor is measured. The interaction is correlated with intraocular pressure.

First, the sensor may be implanted in a patient's eye. This may first involve inserting the sensor into one of the devices described above, such as a Molteno device. Alternatively, the sensor may be encapsulated in other biocompatible material. Implanting the sensor, whether enclosed in a known device or encapsulated in another material, may be carried out according to standard surgical procedures.

As described above, the instrument, including the coil and power source, may provide repetitive bursts of high frequency energy to the implanted sensor. The instrument frequency would be swept over a sufficiently wide range to ensure that the implanted sensor circuit would be induced to "ring" at its resonant frequency.

The present invention permits real-time continuous intraocular pressure data to be measured over any period of time. For example, period of time could cover a twenty-four hour period. In the event the instrument produces analog output, the output could be converted for digital recording on a disk drive. Along these lines, the instrument could be programmed for data acquisition duty cycle. Initial recordings may be duty cycled to obtain both continuous fast-time-response data, such as on the order of less than about 50 msec, and lower resolution average data. Duty cycling may reduce the demand for storage capacity, more in keeping with data capacity on a small, portable self-contained intraocular pressure measurement system. However, this limitation may not be an issue with data that can be real-time routed to high capacity storage via a wireless or wired connection.

The device may be controlled to determine intraocular pressure at regular intervals. The timing of the intervals may vary. One factor that may control the timing of the determination of intraocular pressure is the rate of change of the pressure. Along these lines, if it is determined that the rate of change of the pressure is increasing, then the rate of determination may be increased. Any other regimen may be utilized in controlling the determination of intraocular pressure.

The method can include transmitting the intraocular pressure values, in the form of raw data or after first converted to the actual pressure values, to a processor remote from the instrument. A processor that the values are transmitted or downloaded to could be part of a computer that includes software for determining trendline data, statistical summaries of the maximum and minimum pressures, and/or the percentage of time that the intraocular pressure was "controlled." Sensor performance measurements could include time/frequency response, hysteresis, drift, and stability.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

We claim:

1. A method for measuring intraocular pressure of a patient, the method comprising:

generating a signal with an instrument external to the patient for remotely energizing an in vivo sensor;

measuring interaction between the signal produced by the instrument and the sensor;
correlating the interaction with intraocular pressure;
recording the correlated intraocular pressure;
wherein the instrument generates a signal at varied intervals; and
wherein the interval decreases as a rate of change of intraocular pressure increases.

2. The method according to claim 1, further comprising:
providing an alarm for indicating when intraocular pressure differs from a predetermined value.

* * * * *